United States Patent
McKnight et al.

(10) Patent No.: US 6,566,088 B1
(45) Date of Patent: May 20, 2003

(54) PROLYL-4-HYDROXYLASES

(75) Inventors: Steven L. McKnight, Dallas, TX (US); Richard K. Bruick, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/972,784

(22) Filed: Oct. 4, 2001

(51) Int. Cl.[7] .................................................. C12Q 1/37
(52) U.S. Cl. .......................... 435/24; 435/18; 536/23.2
(58) Field of Search .............................. 435/18, 23, 24, 435/69.1, 252.3; 536/23.2

(56) References Cited

U.S. PATENT DOCUMENTS 4,797,471 A * 1/1989 Teetz et al. .................... 514/18

OTHER PUBLICATIONS

Atreya P. Interaction of Prolyl 4–Hydroxylase with Synthetic Peptide Substrates. J of Biological Chemistry 266(5)2852–8, 1991.*

Asada S. Effect of HSP47 on Prolyl 4–Hydroxylation of Collagen Model Peptides. Cell Structure and Function 24(4)187–196, Aug. 1999.*

Takahashi Y. Hypoxic Induction of Prolyl 4–Hydroxylase I in Cultured Cells. J of Biological Chemistry 275(19)14139–46, May 12, 2000.*

Nissi R. Prolyl 4–Hydroxylase Isoenzymes I and II Have Different Expression Patterns in Several Human Tissues. J of Histochem and Cytochem 49(9)1143–1153, Sep. 2001.*

Epstein A. C. elegans EGL–9 and Mammalian Homologs . . . Cell 107(1)43–54, Oct. 5, 2001.*

* cited by examiner

*Primary Examiner*—Ralph Gitomer
(74) *Attorney, Agent, or Firm*—Richard Aron Osman

(57) ABSTRACT

The invention provides methods and compositions for assaying hypoxia-inducible factor (HIF) prolyl hydroxylation. Subject assays may be cell-based or in vitro, and comprise incubating a mixture comprising an isolated or recombinantly expressed HIF-specific prolyl hydroxylase (HPH), and a substrate of the hydroxylase, under conditions whereby the hydroxylase prolyl hydroxylates the substrate, and detecting a resultant prolyl hydroxylation of the substrate. The mixture may also comprise a candidate agent which modulates the resultant prolyl hydroxylation. In particular embodiments, the hydroxylase is selected from the group consisting of human HPH1, HPH2 and HPH3, and/or the substrate comprises LAPY, wherein P is hydroxylated by the hydroxylase.

24 Claims, 1 Drawing Sheet

Fig. 1

```
HPH 1     1   ----------------------------------------------------------------  ----------------
HPH 2     1   MANDSGGPGGPSPSERDRQYCELCGKMENLLRCSRCRSSFYCCKEHQRQDWKKHKLVCQGSEGALGHGVG
HPH 3     1   ----MDSPCQPQPLSQALPQLPGSSSEPLEPEPGRARMGVESYLPCPLLPSYHCPGVPSEASAGSGT-
dmHPH     1   ----------------------------------------------------------------  ----------------

HPH 1     1   ----------------------------------------------------------------  ----------------
HPH 2    71   PHQHSGPAPPAAVPPPRAGAREPRKAAARRDNASGDAAKG-KVKAKPPADPAAAASPCRAAAGGQGSAVA
HPH 3    64   ---PRATATSTTASPLRDGFGGQDGGELRPLQSEGAAALVTKGCQRLAAQGARPEAPKRKWAEDGGDAPS
dmHPH     1   ----------------------------------------------------------------  ----------------

HPH 1     1   -------------------------------------------MPLGHIMRLDLEKIALEYIVPCLHEVGFCY
HPH 2   140   AEAEPGKEEPPARSSLFQEKANLYPPSNTPGDALSPGGGLRPNGQTKPLPALKLALEYIVPCMNKHGICV
HPH 3   131   PSKRPWARQENQEAEREGGMS-------CSCSSGSGEASAGLMEEALPSAPERLALDYIVPCMRYYGICV
dmHPH     1   -------------------MITSTTTDYKNFFKHSAHPANAEQYFRELLDKRERRYEDLCRNIISDMNQYGLSV

HPH 1    31   LDNFLGEVVGDCVLERVKQLHCTGALRDGQLAGPRAG-----VSKRHLRGDQITWIGGNEEGCEAISFLLS
HPH 2   210   VDDFLGKETGQQIGDEVRALHDTGKFTDGQLVSQKS------DSSKDIRGDKITWIEGKEPGCETIGLLMS
HPH 3   194   KDSFLGAALGGRVLAEVEALKRGGRLRDGQLVSQRA------IPPRSIRGDQIAWVEGHEPGCRSIGALMA
dmHPH    56   VDDFLGMETGLKKILNEVRSMYNAGAFQDGQVTNQTPDAPAVRGDKIRGDKIKWVGGNEPGCSNVWYLTN

HPH 1    97   LIDRLVLYCG-----SRLGKYYVKERSKAMVACYPGNGTGYVRHVDNPNGDGRCITCIYYLNKNWDAKLH
HPH 2   275   SMDDLIRHCN-----GKLGSYKINGRTKAMVACYPGNGTGYVRHVDNPNGDGRCVTCIYYLNKDDAKVS
HPH 3   259   HVDAVIRHCA-----GRLGSYVINGRTKAMVACYPGNGLGYVRHVDNPHGDGRCITCIYYLNQNWDVKVH
dmHPH   126   QIDSVVYRVNTMKDNGILGNYHIRERTRAMVACYPGSGTHYVMHVDNPQKDGRVITAIYYLNINWDARES

HPH 1   162   GGILRIFPEGKSFIADVEPIFDRLLFFWSDRRNPHEVQPSYAMTRYAYTVWYFDAEERAEAKKKFRNLTRK
HPH 2   340   GGILRIFPEGKAQFADIEPKFDRLLFFWSDRRNPHEVQPAYAYTRYAITVWYFDADERARAKVKYLTGEKG
HPH 3   324   GGLLQIFPEGRPVVANIEPLFDRLLIFWSDRRNPHEVKPAYAHTRYAITVWYFDAKERAAAKDKYQLASGQ
dmHPH   196   GGILRIRPTPGTTVADIEPKFDRLIFFWSDIRNPHEVQPAHRTRYAITVWYFDAKEREEALIRAKLENSK

HPH 1   232   TESALTED----------------                                           SEQ ID NO:1
HPH 2   410   VRVELNKPSDSVGKDVF------                                            SEQ ID NO:2
HPH 3   394   KGVQVPVSQPPTPT--------                                             SEQ ID NO:3
dmHPH   266   TNNLAAQAQAQQAEPDSTTTPPAAPASSASSLPVSMSTGTGALNANVSSNSCATSSEICT       SEQ ID NO:4
```

PROLYL-4-HYDROXYLASES

This work was funded in part by a National Research Service Award from the National Institutes of Health and grants from the National Institutes of Health (DK52031 and MH59388). Accordingly, the US government may have rights in this invention.

INTRODUCTION

Field of the Invention

The field of this invention is prolyl-4-hyroxylase assays.

BACKGROUND OF THE INVENTION

The ability of cells to recognize and respond to a low oxygen environment (hypoxia) is critical for the execution of a number of physiological and pathophysiological conditions (1). Almost all mammalian cells express components of a hypoxia response pathway found to be conserved in both flies (2, 3) and worms (4). The hypoxia-inducible transcription factor (HIF), lies at the heart of this pathway. HIF is a heterodimer composed of two members of the basic-Helix-Loop-Helix (bHLH)-containing PER-ARNT-SIM (PAS) domain family; HIF-1α (or the closely related HIF-2α/EPAS-1 or HIF-3α factors) and HIF-1β, also known as the aryl hydrocarbon receptor nuclear translocator (ARNT) (5). Under normoxic conditions HIF-1a is constitutively expressed. However, this subunit is rapidly targeted for proteosome-mediated degradation (6–8) via a protein-ubiquitin ligase complex containing the product of the von Hippel Lindau tumor suppressor protein (pVHL) (9–12). pVHL recognizes the oxygen degradation domain (ODD) of HIF-1α only under normoxic conditions (13–15). Following exposure to a hypoxic environment, this degradation pathway is blocked, allowing HIF-1a accumulation and subsequent movement to the nucleus where it activates hypoxia-responsive genes (reviewed in 16).

Three groups have recently reported that pVHL recognizes the ODD via a conserved proline residue that is hydroxylated exclusively under normoxic conditions (13–15). Examination of cellular extracts prepared under normoxic conditions revealed the presence of a prolyl-4-hydroxylase activity capable of modifying a proline-containing peptide derived from the ODD (13–15). This activity was greatly diminished in extracts prepared under hypoxic conditions or in the presence of "hypoxia mimics" such as $CoCl_2$ or the iron chelator deferoxamine mesylate (13–15). As is the case for known prolyl-4-hydroxylases, this activity was enhanced by supplementation with $Fe^{2+}$, ascorbate and 2-oxoglutarate (14, 15).

The best-characterized prolyl-4-hydroxylase enzymes modify collagen as it matures along its exocytotic pathway (17). These enzymes are typically composed of two a and two b subunits, with the alpha subunit responsible for the prolyl hydroxylase enzymatic activity. A number of lines of evidence rule out these enzymes as the HIF prolyl hydroxylase. First, the substrate context of the modified proline residues in collagen is different from that surrounding the relevant proline residue in HIF (13–15). Second, the collagen-modifying enzymes reside within the endoplasmic reticulum rather than the cytoplasm as expected for the HIF prolyl hydroxylase (17). Finally, two recombinant isoforms of the collagen modifying enzymes expressed from baculovirus were reported to show no activity against the HIF substrate (14).

We disclose here identification of an evolutionarily and structurally conserved family of HIF prolyl hydroxylase (HPH) enzymes. Inappropriate accumulation of HIF resulting from forced expression of the HIF-1a subunit under normoxic conditions was attenuated by co-expression of HPH. Suppression of the *Drosophila melanogaster* HPH enzyme via RNA interference resulted in elevated expression of a hypoxia-inducible gene, LDH, under normoxic conditions. These findings identify an essential component of the hypoxia-response pathway and provide HPH assays for identifying selective modulators of the HPH enzymes, which modulators provide useful leads for therapeutics capable of modulating HIF prolyl hydroxylation and downstream affects, such as angiogenesis.

SUMMARY OF THE INVENTION

The invention provides methods and compositions for assaying hypoxia-inducible factor (HIF) prolyl hydroxylation. In general, the subject assays comprise the steps of: a) incubating a mixture comprising an isolated or recombinantly expressed HIF-specific prolyl hydroxylase (HPH) selected from the group consisting of a human HPH 1, HPH2 and HPH3 prolyl hydroxylase domain, and a substrate of the hydroxylase, under conditions whereby the hydroxylase prolyl hydroxylates the substrate, and b) detecting a resultant prolyl hydroxylation of the substrate. Frequently, the mixture further comprises a candidate agent which modulates the resultant prolyl hydroxylation, wherein an agent-biased prolyl hydroxylation is detected.

In particular embodiments, the hydroxylase is selected from the group consisting of human HPH 1, HPH2 and HPH3, and/or the substrate comprises LAPY (SEQ ID NO:5, residues 7–10), wherein P is hydroxylated by the hydroxylase.

The assays may be cell-based, such as wherein the hydroxylase is recombinantly expressed in the cell and the detecting step comprises detecting a transcriptional reporter of HIF dependent gene expression. Alternatively, the assay may be run in vitro, wherein the hydroxylase is isolated, and the detecting step comprises detecting a reagent which selectively binds the prolyl hydroxylated substrate.

BRIEF DESCRIPTION OF THE DRAWING

FIG. 1. Alignment of human HPH 1, 2 and 3 with the fly dmHPH sequences (SEQ ID NOS:1–4, respectively). Identical residues among all four sequences are shaded in black while similar residues are shaded in gray. Asterisks indicate critical amino acids for $Fe^{2+}$ binding in the corresponding prolyl hydroxylase enzymes that modify collagen.

DESCRIPTION OF PARTICULAR EMBODIMENTS OF THE INVENTION

The invention provides efficient methods of identifying agents, compounds or lead compounds for agents which modulate HPH activity. The methods are amenable to automated, cost-effective high throughput screening of chemical libraries for lead compounds. Identified reagents find use in the pharmaceutical industries for animal and human trials; for example, the reagents may be derivatized and rescreened in in vitro and in vivo assays to optimize activity and minimize toxicity for pharmaceutical development. The subject assays comprise the steps of: a) incubating a mixture comprising an isolated or recombinantly expressed HIF-specific prolyl hydroxylase (HPH) and a substrate of the hydroxylase, under conditions whereby the hydroxylase prolyl hydroxylates the substrate, and b) detecting a resultant prolyl hydroxylation of the substrate.

The recited hydroxylase is selected from the group consisting of a human HPH1, HPH2 and HPH3 prolyl hydroxylase domain. While the native, full-length proteins provide the best model for drugs screens, one may also use truncations of HPH1, HPH2 and HPH3 which retain HPH activity (HIF prolyl hydroxylase domains), which may optionally be coupled to additional homologous (corresponding HPH) or heterologous residues, i.e. the domain may be part of a fusion product with another peptide or polypeptide, e.g. a tag for detection or anchoring, etc. For example, Table 1 shows exemplary hydroxylases comprising a truncated human HPH1, HPH2 and HPH3 which retains assayable HPH activity.

TABLE 1

Exemplary hydroxylases comprising a human HPH1, HPH2 and HPH3 prolyl hydroxylase domain

| Hydroxylase | Structure | HPH Activity |
| --- | --- | --- |
| HPH1ΔN | SEQ ID NO: 1, residues 9–232 | +++ |
| HPH1ΔC | SEQ ID NO: 1, residues 1–224 | +++ |
| His-HPH1ΔN | N-(His)$_6$-HPH1ΔN | +++ |
| Gal4-HPH1ΔN | N-Gal4-HPH1ΔN | +++ |
| HPH2ΔN | SEQ ID NO: 2, residues 161–410 | +++ |
| HPH2ΔNC | SEQ ID NO: 2, residues 136–381 | +++ |
| HPH3ΔN | SEQ ID NO: 3, residues 146–394 | +++ |
| HPH3ΔNC | SEQ ID NO: 3, residues 124–388 | +++ |

The mixture also comprises a substrate which is prolyl hydroxylated by the recited hydroxylase. Suitable peptide substrates are readily identified in the subject prolyl hydroxylase screening assays. Screening source material may be random sequence prolyl peptides, or libraries derived from directed or random mutation of a human HIF-1α oxygen degradation domain (ODD) peptide comprising Pro564 (see, experimental, below, and Jaakkola et al. and Ivan et al., below). For example, in some experiments below, we effected a double Met to Ala substitution to provide an equivalent HDH substrate with less oxidative reactivity and hence, improved compatibility with mass spectroscopy-based analysis. In general, preferred substrates comprise the peptide LAPY, more preferably LAPYI (SEQ ID NO:5, residues 7–11), more preferably LAPYI, wherein the I is coupled to an additional residue, preferably P or G (see, experimental, below). In particular embodiments, the substrate comprises a detectable label, which may be directly detectable (e.g. radiolabels, fluorescent labels, etc.) or indirectly detectable (e.g. epitope tags, biotin, etc.).

Frequently, the mixture further comprises a candidate agent which modulates the resultant prolyl hydroxylation, wherein an agent-biased prolyl hydroxylation is detected. Candidate agents encompass numerous chemical classes, though typically they are organic compounds; preferably small organic compounds and are obtained from a wide variety of sources including libraries of synthetic or natural compounds. A variety of other reagents may also be included in the mixture. These include reagents like cofactors (e.g. Fe(II)), cosubstrates (e.g. dioxygen), salts, buffers, neutral proteins, e.g. albumin, detergents, protease inhibitors, antimicrobial agents, etc.

The assays may also employ known modulators for a variety of purposes, such as comparative or competitive analysis. For example, dimethyl-oxalylglycine is a competitive inhibitor by virtue of its similarity to the cosubstrate, 2-oxoglutarate. Similarly, ascorbate is shown to promote the reaction, and a variety of analogs of 2-oxaglutarate or ascorbate inhibit assay prolyl hydroxylation. In addition, divalent metal ions such as Co+2 can compete with $Fe^{2+}$ for occupancy and inhibit hydroxylation and iron chelators like deferoxamine mesylate inhibit hydroxylation by competing for $Fe^{2+}$. Finally, suicide inhibitors are readily constructed by incorporating oxaproline residue into the hydroxylase substrate, e.g. Wu et al., 1999, J Am Chem Soc 121, 587–588.

The assays may be cell-based, such as wherein the hydroxylase is recombinantly expressed in the cell and the detecting step comprises detecting a transcriptional reporter of HIF dependent gene expression (see, e.g. experimental, below). Alternatively, the assay may be run in vitro, wherein the hydroxylase is isolated and preferably provided in a predetermined amount. For in vitro assays, hydroxylation may be detected directly or indirectly. For example, hydroxylation may be directly detected in mass spectroscopy-based assays. Alternatively, the hydroxylation may be detected with a reagent which selectively binds the prolyl hydroxylated substrate, wherein depending on the reagent, the binding may be detected by changes in fluorescent polarization, fluorescence, radiation, catalytic product (e.g. luciferase, galactosidase, etc.), etc.

The subject compositions include systems and kits for the disclosed HIF-specific prolyl hydroxylation assays. For in vitro assays, for example, such systems and kits comprise predetermined amounts of the isolated hydroxylase and of one or more suitable substrates. The systems and kits will generally also comprise further reagents described herein to facilitate the reaction, suitable packaging, and written instructions describing the hydroxylase, the substrate and the assay.

The following experimental examples section is offered by way of illustration and not by way of limitation.

DETAILED EXPERIMENTAL EXAMPLES

To identify novel prolyl-4-hydroxylase enzymes, we queried the Genbank database for sequences related to the catalytic α subunit of the collagen-modifying prolyl-4-hydroxylases. Of the several families of putative prolyl-hydroxylase enzymes thus identified, five contained human homologues. Furthermore, the amino acid sequences of each of these families contained conserved amino acid residues believed to bind $Fe^{2+}$ and 2-oxoglutarate (17).

In order to investigate whether any of these candidate enzymes might specify HIF-1a-directed prolyl hydroxylase activity, we cloned a representative member of each family into the pcDNA3.1/V5-His expression vector (18). These five polypeptides, designated candidates A, B, C, D and one candidate subsequently designated HIF prolyl hydroxylase 1 (HPH 1), were in vitro transcribed/translated in a rabbit reticulocyte lysate system. To measure prolyl hydroxylase activity (19), the translation products were incubated in the presence of ascorbate, 2-oxoglutarate, and $FeSO_4$ with a biotinylated peptide derived from the human HIF-1a ODD that contains the target proline residue (Biotin-Acp-DLDLEALAP*YIPADDDFQL; SEQ ID NO:5). When this proline residue (P*) is hydroxylated, this peptide can be recognized as a substrate for [$^{35}$S]-labeled human pVHL (13–15). Streptavidin-coated agarose beads were used to precipitate [$^{35}$S]-labeled human pVHL associated with the biotinylated peptide and measured by scintillation counting. Minimal prolyl hydroxylase activity was observed in rabbit reticulocyte lysate programmed to express a Lac Z control, demonstrating that the majority of endogenous prolyl hydroxylase activity reported for reticulocyte lysate is inactivated during the 1 hr in vitro transcription/translation incubation at 30° C. Of the five candidate enzymes assayed, only one, HPH-1, was able to enhance pVHL association with the biotinylated peptide. In addition to HPH 1, the human genome encodes two highly related HPH 1 paralogs, designated HPH 2 and HPH 3 (FIG. 1). As with HPH 1, both of these enzymes were observed to catalyze the hydroxylation of the key proline residue in the HIF-1a peptide substrate as measured by the [$^{35}$S]-pVHL pull-down assay.

Several amino acid residues have been shown through site-directed mutagenesis studies to be involved in coordinating $Fe^{2+}$ within the active site of the collagen-modifying prolyl-4-hydroxylases (17). These same residues are also present in the HPH enzymes (indicated by * in FIG. 1). To test the role of these residues in HPH 1-mediated proline hydroxylation, $His^{135}$, $Asp^{137}$ and $His^{196}$ were individually changed to alanine (H135A, D137A and H196A respectively). Each of these mutations eliminated the prolyl hydroxylase activity of the native HPH 1 enzyme.

We next expressed the human HPH enzymes in bacterial cells such that they could be purified by affinity chromatography as soluble proteins (20). Purified HPH 2 was able to hydroxylate the HIF-1a peptide substrate. The activity of this recombinant protein was greatly stimulated by the addition of ascorbate, 2-oxoglutarate and $FeSO_4$. Furthermore, the activity of the HPH 2 enzyme was inhibited by an excess of $CoCl_2$. $CoCl_2$ is known to induce the hypoxic response pathway by stabilizing HIF under normoxic conditions, possibly by competing with $Fe^{2+}$ for occupancy within the active site of HPH. Together, our data demonstrate that HPH 1, 2 and 3 are natural prolyl hydroxylase enzymes which modify the proline residue within the HIF-1a ODD to mobilize pVHL binding.

Previous studies have indicated that amino acids in close proximity to the proline residue targeted for hydroxylation ($Pro^{564}$ in human HIF-1a) influence HIF-1a modification/pVHL binding. Specifically, mutation of $Leu^{562}$ to Ala (13), $Ala^{563}$ to Gly (15) and $Tyr^{565}$ to Ala (14) have been shown to prevent prolyl hydroxylation by the endogenous HIF prolyl hydroxylase activity present in cellular extracts. Conversely, mutation of $Pro^{567}$ to Gly has been shown to exert a slight stimulatory effect in pVHL pull-down assays (14). In order to examine the substrate specificity of HPH 1, individual biotinylated peptide substrates were synthesized to contain each of these four point mutations. To discriminate the affects of these mutations on pVHL binding from their affects on proline hydroxylation, each peptide was also synthesized with the proline residue ($Pro^{564}$) already hydroxylated. Fully hydroxylated peptides corresponding to the wild type and variant ODD sequences were all recognized by [$^{35}$S]-pVHL, though the A563G and Y565A mutations did partially compromise pVHL association. As reported for the endogenous HIF prolyl hydroxylase, HPH 1 generated via in vitro transcription/translation, as well as recombinant HPH 2 purified from E. coli, were unable to modify peptides containing the L562A, A563G or Y565A mutations. However, a peptide containing a mutation of $Pro^{567}$ to glycine served as an equal, if not better, substrate for the human HPH enzymes.

These data demonstrate that HPH 1, 2 and 3 are prolyl hydroxylase enzymes that share a similar substrate specificity with the endogenous HIF prolyl hydroxylase. To test whether these HPH enzymes represent part of the hypoxic response pathway in vivo we first co-transfected (21) human embryonic kidney 293 cells with a hypoxia-responsive luciferase reporter (22) and increasing amounts of a vector expressing human HIF-1a under the control of the constitutive CMV promoter. Forced overexpression of HIF-1a can overcome the degradation pathway, resulting in accumulation of the HIF transcription factor under normoxic conditions and subsequent induction of the HRE-containing HIF reporter gene (22). Induction of the HIF-dependent luciferase reporter by either 30 ng or 100 ng of HIF-1a expression vector was not affected by co-transfection of 3 ng of CMV-driven vectors expressing Lac Z or candidates A, B, C, and D. By contrast, HPH 1 was able to attenuate HIF-1a activation of the HRE-driven reporter as expected if HIF prolyl hydroxylase activity was rate-limiting for HIF-1a degradation under these conditions. Mutation of $His^{135}$, $Asp^{137}$ or $His^{196}$ to alanine eliminated the interfering activity of HPH 1 in these transfection assays. Neither HPH 1 nor the other candidate enzymes were observed to affect expression of a constitutive, CMV-driven luciferase reporter, demonstrating that HPH 1 specifically attenuates HIF-1a-mediated induction of the hypoxia-responsive reporter. Finally, the ability of HPH 1 to diminish induction of the HIF-responsive luciferase reporter was lost when cells were incubated in an atmosphere containing 0.5% $O_2$. These data indicate that the transiently overexpressed HPH 1 enzyme is subject to inhibition by a low oxygen environment.

It is logical to anticipate that overexpression of HPH should suppress the hypoxia response system. Likewise, inhibition of HPH should activate the hypoxia response pathway under normoxic conditions. A single D. melanogaster HPH enzyme was identified within the fly genome (encoded by gene CG1114 and hereby designated dmHPH). Fly genes corresponding to HIF-1a (Sima), ARNT (dARNT) and VHL (dVHL) have been previously identified (2, 3, 23, 24). Furthermore, the activity/stability of Sima has been shown to be regulated in response to hypoxia (2). Together, these observations suggest that fly cells contain a hypoxic response pathway analogous to mammalian cells. We incubated double-stranded RNAs corresponding to Sima or dmHPH with the D. melanogaster KC167 cell line in order to eliminate expression of these genes by RNA interference (25). Following prolonged incubation of KC167 cells with these double stranded RNAs under normoxic conditions, total RNA was prepared and examined by Northern blotting. At the level of detection afforded by Northern blot analysis, RNA interference with double stranded RNA substantially reduced the levels of mRNAs encoding either Sima or dmHPH.

To follow the affects of the partial loss of function of these gene products we examined the expression of the fly gene encoding lactate dehydrogenase (dmLDH). LDH has been identified as a HIF-dependent hypoxia-inducible gene in mammalian cells (26, 27). Likewise, untreated KC167 cells incubated in 1% $O_2$ for 15 hr express 7.5 times more dmLDH mRNA than cells maintained under normoxic conditions (20% $O_2$). KC167 cells treated with double-stranded Sima RNA suffered a two-fold reduction in dmLDH mRNA levels. By contrast, RNAi-mediated reduction of dmHPH mRNA resulted in a 2.5× increase in dmLDH mRNA levels under normoxic conditions.

The data presented here demonstrate that the human HPH 1, 2, and 3 enzymes hydroxylate the critical proline residue within the HIF-1a ODD. It is further shown that overexpression of HPH 1 attenuates HIF-1a-mediated gene activation in mammalian cells, and that RNAi-mediated elimination of dmHPH elevates expression of a hypoxia-inducible gene under normoxic conditions in cultured KC167 cells. We conclude that HPH enzymes represent bona fide natural HIF prolyl hydroxylases and act as integral regulators of the HIF-dependent hypoxia response pathway.

Previous studies have reported on the molecular biological properties of a rat homolog of HPH 1. Overexpression of this protein, designated SM-20, has been reported to result in cell death (28). Although our own studies have not been designed to pursue this observation, it is important to point out that the ability of HPH 1 to attenuate HIF-1a-induction of the hypoxia-responsive luciferase reporter is not attributable to its effect on cell viability. Co-transfection of HPH 1 with a CMV-driven luciferase reporter did not attenuate luciferase expression. Moreover, HPH 1 did not attenuate the HRE-driven luciferase reporter under hypoxic culture conditions. Finally, visual inspection of cell cultures transfected with our HPH 1 expression vector has given no overt evidence of programmed cell death.

These studies identify the three human HPH enzymes as attractive targets for the identification of unique therapeutic chemicals. It has recently been reported that transgenic expression of a modified form of HIF-1a lacking the ODD in basal keratinocytes results in increased dermal vascularization (29). The vascular bed formed under such conditions is stable and lacks the associated edema, inflammation and spontaneous hemorrhagic ulcers that accompany leaky vasculature resulting from the singular expression of vasculogenic growth factors such as VEGF (30–32). The more substantive neovascularization resulting from constitutive HIF-1a expression may reflect the fact that this transcription factor activates not only VEGF gene expression but also other genes important for the formation of new blood vessels (reviewed in 33). Hence, selective inhibitors of the HPH enzymes provide useful leads for therapeutics capable of promoting angiogenesis.

REFERENCES AND NOTES

1. G. L. Semenza, *Genes Dev.* 14, 1983 (2000).
2. N. C. Bacon et al., *Biochem. Biophys. Res. Comm.* 249, 811 (1998).
3. J. R. Nambu, W. Chen, S. Hu, S. T. Crews, *Gene* 172, 249 (1996).
4. H. Jiang, R. Guo, J. Powell-Coffman, *Proc. Natl. Acad. Sci. U.S.A.* 98, 7916 (2001).
5. G. L. Wang, B. H. Jiang, E. A. Rue, G. L. Semenza, *Proc. Natl. Acad. Sci. U.S.A.* 92, 5510 (1995).
6. L. E. Huang, J. Gu, M. Schau, H. F. Bunn, *Proc. Natl. Acad. Sci. U.S.A.* 95, 7987 (1998).
7. P. J. Kallio, W. J. Wilson, S. O'Brien, Y. Makino, L. Poellinger, *J. Biol. Chem.* 274, 6519 (1999).
8. S. Salceda, J. Caro, *J. Biol. Chem.* 272, 22642 (1997).
9. M. E. Cockman et al., *J. Biol. Chem.* 275, 25733 (2000).
10. P. H. Maxwell et al., *Nature* 399, 271 (1999).
11. M. Ohh et al., *Nature Cell Biol.* 2, 423 (2000).
12. K. Tanimoto, Y. Makino, T. Pereira, L. Poellinger, *EMBO J.* 19, 4298 (2000).
13. M. Ivan et al., *Science* 292, 464 (2001).
14. P. Jaakkola et al., *Science* 292, 468 (2001).
15. F. Yu, S. B. White, F. S. Lee, *Proc. Natl. Acad. Sci. U.S.A.* 98, 9630 (2001).
16. G. L. Semenza, *Annu. Rev. Cell Dev. Biol.* 15, 551 (1999).
17. K. I. Kivirikko, T. Pihlajaniemi, in *Advances in Enzymology and Related Areas of Molecular Biology*, D. L. Purich, Ed. (John Wiley & Sons, Inc., 1998), vol. 72, pp. 325–398.
18. Coding regions were amplified by RT-PCR from total RNA prepared from human cell lines using oligonucleotides derived from the following sequences (Genbank accession number: HPH 1 (XM_012332); HPH 2 (AF229245); HPH 3 (BC001723); candidate A (NM_017732); candidate B (AK022130); candidate C (AK001580); candidate D (AK023553). A splice-variant of HPH 2 was used in which residues 76–177 are omitted. Point mutations to HPH 1 were generated by PCR. Each cDNA was cloned into the pcDNA3.1/V5-HIS vector (Invitrogen Corp.) in frame with the carboxy-terminal V5-HIS tag.
19. Candidate polypeptides were synthesized using the TNT Coupled Reticulocyte Lysate System (Promega) for 1 hr at 30° C. Expression of each gene product was confirmed by Western blot analysis using an antibody specific for the carboxy-terminal V5 tag. 12.5 $\mu$l of each in vitro transcription/translation reaction was incubated for 30 min at 30° C. in a reaction buffer containing 20 mM Tris-Cl (pH 7.5), 5 mM KCl, 1.5 mM $MgCl_2$, 1 mM DTT, 2 mM 2-oxoglutarate, 2 mM ascorbate and 250 $\mu$M $FeSO_4$ in the presence of 30 $\mu$l ImunoPure Immobilized Streptavidin beads that had previously been incubated with 1 $\mu$g of peptide for 30 min at room temperature and washed 3× to remove excess peptide. Following incubation, the beads were washed 3× with 1 ml cold NTEN buffer (20 mM Tris-Cl (pH 8.0), 100 mM NaCl, 1 mM EDTA and 0.5% NP-40) and incubated for 10 min at 4° C. with approximately 35 kcpm of [$^{35}$S]-labeled human VHL in 500 $\mu$l EBC buffer (50 mM Tris-Cl (pH 8.0), 120 mM NaCl, 0.5% NP-40). The beads were washed 3× with cold NTEN buffer and bound [$^{35}$S] was measured by scintillation counting. [$^{35}$S]-labeled human VHL was synthesized from the human VHL cDNA cloned into the pcDNA3.1/V5-HIS vector (Invitrogen Corp.) using the TNT Coupled Reticulocyte Lysate System (Promega) and [$^{35}$S]-L-Met (Amersham Pharmacia Biotech) and desalted using a PD-10 column (Amersham Pharmacia Biotech).
20. HPH 2 was cloned into the pMBP-parallell vector (34) and expressed in the BL21-CodonPlus-RIL *E. coli* strain (Stratagene). Recombinant protein was purified by virtue of the amino-terminal MBP protein using amylose resin (New England Biolabs) and eluted in the presence of 10 mM maltose.
21. Transfection experiments were performed as in (22) with DNA amounts indicated in the text. Western blot analysis using an antibody specific for the carboxy-terminal V5 tag was used to confirm expression of each polypeptide following transfection of 1 $\mu$g of each expression vector.
22. R. K. Bruick, *Proc. Natl. Acad. Sci. U.S.A.* 97, 9082 (2000).
23. B. Adryan, H.-J. Decker, T. S. Papas, T. Hsu, *Oncogene* 19, 2803 (2000).
24. E. Ma, G. G. Haddad, *Mol. Brain Res.* 73, 11 (1999).
25. KC167 cells were maintained at 24° C. in CCM 3 media (HyClone). Cells were treated as follows: initially 4×10$^5$ KC167 cells were incubated for seven days in the presence of 25 $\mu$g double stranded RNAs of approximately 700 base pairs in length generated using the T7 MEGAscript Kit (Ambion) with double-stranded RNA refreshed daily. Cells were incubated under normoxic (20% $O_2$) or hypoxic (1% $O_2$, 99% $N_2$) conditions for an additional 15 hr and total RNA was prepared using RNA STAT-60 (Tel-Test, Inc.). RNAs were resolved by electrophoresis in a 1.2% agarose gel in the presence of 1.8% formaldehyde, transferred to nitrocellulose filters, and hybridized with the indicated $^{32}$P-labeled DNA probes.
26. N. V. Iyer et al., *Genes Dev.* 12, 149 (1998).
27. H. E. Ryan, J. Lo, R. S. Johnson, *EMBO J* 17, 3005 (1998).
28. E. A. Lipscomb, P. D. Sarmiere, R. S. Freeman, *J. Biol. Chem.* 276, 5085 (2001).
29. D. A. Elson et al., *Genes Dev.* 15, (2001).

30. M. Detmar et al., *J. Invest. Dermatol.* 111, 1 (1998).
31. F. Larcher, R. Murillas, M. Bolontrade, C. J. Conti, J. L. Jorcano, *Oncogene* 17, 303 (1998).
32. G. Thurston et al., *Science* 286, 2511 (1999).
33. R. K. Bruick, S. L. McKnight, *Genes Dev.* 15, (2001).
34. P. Sheffield, S. Garrard, Z. Derewenda, *Prot. Express. Pur.* 15, 34 (1999).

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A hypoxia-inducible factor (HIF) prolyl hydroxylation assay, comprising the steps of:
   a) incubating a mixture comprising an isolated or recombinantly expressed HIF-specific prolyl hydroxylase (HPH) selected from the group consisting of a human HPH1, HPH2 and HPH3 prolyl hydroxylase domain, annd a peptide substrate of the hydroxylase, under conditions whereby the hydroxylase prolyl hydroxylates the substrate, and
   b) detecting a resultant prolyl hydroxylation of the substrate, which provides an assay readout of the HPH.

2. The assay of claim 1, wherein the mixture further comprises a candidate agent which modulates the resultant prolyl hydroxylation.

3. The assay of claim 2, wherein the hydroxylase is selected from the group consisting of human HPH1, HPH2 and HPH3.

4. The assay of claim 3, wherein the substrate comprises LAPY, wherein P is hydroxylated by the hydroxylase.

5. The assay of claim 4, wherein the hydroxylase is recombinantly expressed in a cell and the detecting step comprises detecting a transcriptional reporter of HIF dependent gene expression.

6. The assay of claim 4, wherein the hydroxylase is isolated, and the detecting step comprises detecting a reagent which selectively binds the prolyl hydroxylated substrate.

7. The assay of claim 3, wherein the hydroxylase is recombinantly expressed in a cell and the detecting step comprises detecting a transcriptional reporter of HIF dependent gene expression.

8. The assay of claim 3, wherein the hydroxylase is isolated, and the detecting step comprises detecting a reagent which selectively binds the prolyl hydroxylated substrate.

9. The assay of claim 2, wherein the substrate comprises LAPY, wherein P is hydroxylated by the hydroxylase.

10. The assay of claim 9, wherein the hydroxylase is recombinantly expressed in a cell and the detecting step comprises detecting a transcriptional reporter of HIF dependent gene expression.

11. The assay of claim 9, wherein the hydroxylase is isolated, and the detecting step comprises detecting a reagent which selectively binds the prolyl hydroxylated substrate.

12. The assay of claim 2, wherein the hydroxylase is recombinantly expressed in a cell and the detecting step comprises detecting a transcriptional reporter of HIF dependent gene expression.

13. The assay of claim 2, wherein the hydroxylase is isolated, and the detecting step comprises detecting a reagent which selectively binds the prolyl hydroxylated substrate.

14. The assay of claim 1, wherein the hydroxylase is selected from the group consisting of human HPH1, HPH2 and HPH3.

15. The assay of claim 14, wherein the substrate comprises LAPY, wherein P is hydroxylated by the hydroxylase.

16. The assay of claim 15, wherein the hydroxylase is recombinantly expressed in a cell and the detecting step comprises detecting a transcriptional reporter of HIF dependent gene expression.

17. The assay of claim 15, wherein the hydroxylase is isolated, and the detecting step comprises detecting a reagent which selectively binds the prolyl hydroxylated substrate.

18. The assay of claim 14, wherein the hydroxylase is recombinantly expressed in a cell and the detecting step comprises detecting a transcriptional reporter of HIF dependent gene expression.

19. The assay of claim 14, wherein the hydroxylase is isolated, and the detecting step comprises detecting a reagent which selectively binds the prolyl hydroxylated substrate.

20. The assay of claim 1, wherein the substrate comprises LAPY (SEQ ID NO:5, residues 7–10), wherein P is hydroxylated by the hydroxylase.

21. The assay of claim 20, wherein the hydroxylase is recombinantly expressed in a cell and the detecting step comprises detecting a transcriptional reporter of HIF dependent gene expression.

22. The assay of claim 20, wherein the hydroxylase is isolated, and the detecting step comprises detecting a reagent which selectively binds the prolyl hydroxylated substrate.

23. The assay of claim 1, wherein the hydroxylase is recombinantly expressed in a cell and the detecting step comprises detecting a transcriptional reporter of HIF dependent gene expression.

24. The assay of claim 1, wherein the hydroxylase is isolated, and the detecting step comprises detecting a reagent which selectively binds the prolyl hydroxylated substrate.

* * * * *

SEQUENCE LISTING

<160> NUMBER OF SEQ ID NOS: 5

<210> SEQ ID NO 1
<211> LENGTH: 239
<212> TYPE: PRT
<213> ORGANISM: human

<400> SEQUENCE: 1

```
Met Pro Leu Gly His Ile Met Arg Leu Asp Leu Glu Lys Ile Ala Leu
1               5                   10                  15

Glu Tyr Ile Val Pro Cys Leu His Glu Val Gly Phe Cys Tyr Leu Asp
            20                  25                  30

Asn Phe Leu Gly Glu Val Val Gly Asp Cys Val Leu Glu Arg Val Lys
        35                  40                  45

Gln Leu His Cys Thr Gly Ala Leu Arg Asp Gly Gln Leu Ala Gly Pro
    50                  55                  60

Arg Ala Gly Val Ser Lys Arg His Leu Arg Gly Asp Gln Ile Thr Trp
65                  70                  75                  80

Ile Gly Gly Asn Glu Glu Gly Cys Glu Ala Ile Ser Phe Leu Leu Ser
                85                  90                  95

Leu Ile Asp Arg Leu Val Leu Tyr Cys Gly Ser Arg Leu Gly Lys Tyr
            100                 105                 110

Tyr Val Lys Glu Arg Ser Lys Ala Met Val Ala Cys Tyr Pro Gly Asn
        115                 120                 125

Gly Thr Gly Tyr Val Arg His Val Asp Asn Pro Asn Gly Asp Gly Arg
    130                 135                 140

Cys Ile Thr Cys Ile Tyr Tyr Leu Asn Lys Asn Trp Asp Ala Lys Leu
145                 150                 155                 160

His Gly Gly Ile Leu Arg Ile Phe Pro Glu Gly Lys Ser Phe Ile Ala
                165                 170                 175

Asp Val Glu Pro Ile Phe Asp Arg Leu Leu Phe Phe Trp Ser Asp Arg
            180                 185                 190

Arg Asn Pro His Glu Val Gln Pro Ser Tyr Ala Thr Arg Tyr Ala Met
        195                 200                 205

Thr Val Trp Tyr Phe Asp Ala Glu Glu Arg Ala Glu Ala Lys Lys Lys
    210                 215                 220

Phe Arg Asn Leu Thr Arg Lys Thr Glu Ser Ala Leu Thr Glu Asp
225                 230                 235
```

<210> SEQ ID NO 2
<211> LENGTH: 426
<212> TYPE: PRT
<213> ORGANISM: human

<400> SEQUENCE: 2

```
Met Ala Asn Asp Ser Gly Gly Pro Gly Gly Pro Ser Pro Ser Glu Arg
1               5                   10                  15
```

-continued

```
Asp Arg Gln Tyr Cys Glu Leu Cys Gly Lys Met Glu Asn Leu Leu Arg
             20                  25                  30
Cys Ser Arg Cys Arg Ser Ser Phe Tyr Cys Cys Lys Glu His Gln Arg
         35                  40                  45
Gln Asp Trp Lys Lys His Lys Leu Val Cys Gln Gly Ser Glu Gly Ala
     50                  55                  60
Leu Gly His Gly Val Gly Pro His Gln His Ser Gly Pro Ala Pro Pro
 65                  70                  75                  80
Ala Ala Val Pro Pro Arg Ala Gly Ala Arg Glu Pro Arg Lys Ala
                 85                  90                  95
Ala Ala Arg Arg Asp Asn Ala Ser Gly Asp Ala Ala Lys Gly Lys Val
             100                 105                 110
Lys Ala Lys Pro Pro Ala Asp Pro Ala Ala Ala Ser Pro Cys Arg
         115                 120                 125
Ala Ala Ala Gly Gly Gln Gly Ser Ala Val Ala Ala Glu Ala Glu Pro
     130                 135                 140
Gly Lys Glu Glu Pro Pro Ala Arg Ser Ser Leu Phe Gln Glu Lys Ala
145                 150                 155                 160
Asn Leu Tyr Pro Pro Ser Asn Thr Pro Gly Asp Ala Leu Ser Pro Gly
                 165                 170                 175
Gly Gly Leu Arg Pro Asn Gly Gln Thr Lys Pro Leu Pro Ala Leu Lys
             180                 185                 190
Leu Ala Leu Glu Tyr Ile Val Pro Cys Met Asn Lys His Gly Ile Cys
         195                 200                 205
Val Val Asp Asp Phe Leu Gly Lys Glu Thr Gly Gln Gln Ile Gly Asp
     210                 215                 220
Glu Val Arg Ala Leu His Asp Thr Gly Lys Phe Thr Asp Gly Gln Leu
225                 230                 235                 240
Val Ser Gln Lys Ser Asp Ser Ser Lys Asp Ile Arg Gly Asp Lys Ile
                 245                 250                 255
Thr Trp Ile Glu Gly Lys Glu Pro Gly Cys Glu Thr Ile Gly Leu Leu
             260                 265                 270
Met Ser Ser Met Asp Asp Leu Ile Arg His Cys Asn Gly Lys Leu Gly
         275                 280                 285
Ser Tyr Lys Ile Asn Gly Arg Thr Lys Ala Met Val Ala Cys Tyr Pro
     290                 295                 300
Gly Asn Gly Thr Gly Tyr Val Arg His Val Asp Asn Pro Asn Gly Asp
305                 310                 315                 320
Gly Arg Cys Val Thr Cys Ile Tyr Tyr Leu Asn Lys Asp Trp Asp Ala
                 325                 330                 335
Lys Val Ser Gly Gly Ile Leu Arg Ile Phe Pro Glu Gly Lys Ala Gln
             340                 345                 350
Phe Ala Asp Ile Glu Pro Lys Phe Asp Arg Leu Leu Phe Phe Trp Ser
         355                 360                 365
Asp Arg Arg Asn Pro His Glu Val Gln Pro Ala Tyr Ala Thr Arg Tyr
     370                 375                 380
Ala Ile Thr Val Trp Tyr Phe Asp Ala Asp Glu Arg Ala Arg Ala Lys
385                 390                 395                 400
Val Lys Tyr Leu Thr Gly Glu Lys Gly Val Arg Val Glu Leu Asn Lys
                 405                 410                 415
Pro Ser Asp Ser Val Gly Lys Asp Val Phe
                 420                 425
```

```
<210> SEQ ID NO 3
<211> LENGTH: 407
<212> TYPE: PRT
<213> ORGANISM: human

<400> SEQUENCE: 3

Met Asp Ser Pro Cys Gln Pro Gln Pro Leu Ser Gln Ala Leu Pro Gln
 1               5                  10                  15

Leu Pro Gly Ser Ser Glu Pro Leu Glu Pro Glu Pro Gly Arg Ala
            20                  25                  30

Arg Met Gly Val Glu Ser Tyr Leu Pro Cys Pro Leu Leu Pro Ser Tyr
            35                  40                  45

His Cys Pro Gly Val Pro Ser Glu Ala Ser Ala Gly Ser Gly Thr Pro
    50                  55                  60

Arg Ala Thr Ala Thr Ser Thr Thr Ala Ser Pro Leu Arg Asp Gly Phe
65                  70                  75                  80

Gly Gly Gln Asp Gly Gly Glu Leu Arg Pro Leu Gln Ser Glu Gly Ala
                85                  90                  95

Ala Ala Leu Val Thr Lys Gly Cys Gln Arg Leu Ala Ala Gln Gly Ala
            100                 105                 110

Arg Pro Glu Ala Pro Lys Arg Lys Trp Ala Glu Asp Gly Gly Asp Ala
        115                 120                 125

Pro Ser Pro Ser Lys Arg Pro Trp Ala Arg Gln Glu Asn Gln Glu Ala
130                 135                 140

Glu Arg Glu Gly Gly Met Ser Cys Ser Cys Ser Ser Gly Ser Gly Glu
145                 150                 155                 160

Ala Ser Ala Gly Leu Met Glu Glu Ala Leu Pro Ser Ala Pro Glu Arg
                165                 170                 175

Leu Ala Leu Asp Tyr Ile Val Pro Cys Met Arg Tyr Tyr Gly Ile Cys
            180                 185                 190

Val Lys Asp Ser Phe Leu Gly Ala Ala Leu Gly Gly Arg Val Leu Ala
        195                 200                 205

Glu Val Glu Ala Leu Lys Arg Gly Gly Arg Leu Arg Asp Gly Gln Leu
    210                 215                 220

Val Ser Gln Arg Ala Ile Pro Pro Arg Ser Ile Arg Gly Asp Gln Ile
225                 230                 235                 240

Ala Trp Val Glu Gly His Glu Pro Gly Cys Arg Ser Ile Gly Ala Leu
                245                 250                 255

Met Ala His Val Asp Ala Val Ile Arg His Cys Ala Gly Arg Leu Gly
            260                 265                 270

Ser Tyr Val Ile Asn Gly Arg Thr Lys Ala Met Val Ala Cys Tyr Pro
        275                 280                 285

Gly Asn Gly Leu Gly Tyr Val Arg His Val Asp Asn Pro His Gly Asp
    290                 295                 300

Gly Arg Cys Ile Thr Cys Ile Tyr Tyr Leu Asn Gln Asn Trp Asp Val
305                 310                 315                 320

Lys Val His Gly Gly Leu Leu Gln Ile Phe Pro Glu Gly Arg Pro Val
                325                 330                 335

Val Ala Asn Ile Glu Pro Leu Phe Asp Arg Leu Leu Ile Phe Trp Ser
            340                 345                 350

Asp Arg Arg Asn Pro His Glu Val Lys Pro Ala Tyr Ala Thr Arg Tyr
        355                 360                 365

Ala Ile Thr Val Trp Tyr Phe Asp Ala Lys Glu Arg Ala Ala Ala Lys
    370                 375                 380
```

-continued

Asp Lys Tyr Gln Leu Ala Ser Gly Gln Lys Gly Val Gln Val Pro Val
385                 390                 395                 400

Ser Gln Pro Pro Thr Pro Thr
            405

<210> SEQ ID NO 4
<211> LENGTH: 325
<212> TYPE: PRT
<213> ORGANISM: Drosophila melanogaster

<400> SEQUENCE: 4

Met Ile Thr Ser Thr Thr Thr Asp Tyr Lys Asn Phe Phe Lys His Ser
  1               5                  10                  15

Ala His Pro Ala Asn Ala Glu Gln Tyr Phe Arg Glu Leu Leu Asp Lys
                 20                  25                  30

Arg Glu Arg Arg Tyr Glu Asp Leu Cys Arg Asn Ile Ile Ser Asp Met
             35                  40                  45

Asn Gln Tyr Gly Leu Ser Val Val Asp Asp Phe Leu Gly Met Glu Thr
         50                  55                  60

Gly Leu Lys Ile Leu Asn Glu Val Arg Ser Met Tyr Asn Ala Gly Ala
 65                  70                  75                  80

Phe Gln Asp Gly Gln Val Val Thr Asn Gln Thr Pro Asp Ala Pro Ala
                 85                  90                  95

Val Arg Gly Asp Lys Ile Arg Gly Asp Lys Ile Lys Trp Val Gly Gly
            100                 105                 110

Asn Glu Pro Gly Cys Ser Asn Val Trp Tyr Leu Thr Asn Gln Ile Asp
            115                 120                 125

Ser Val Val Tyr Arg Val Asn Thr Met Lys Asp Asn Gly Ile Leu Gly
        130                 135                 140

Asn Tyr His Ile Arg Glu Arg Thr Arg Ala Met Val Ala Cys Tyr Pro
145                 150                 155                 160

Gly Ser Gly Thr His Tyr Val Met His Val Asp Asn Pro Gln Lys Asp
                165                 170                 175

Gly Arg Val Ile Thr Ala Ile Tyr Tyr Leu Asn Ile Asn Trp Asp Ala
            180                 185                 190

Arg Glu Ser Gly Gly Ile Leu Arg Ile Arg Pro Thr Pro Gly Thr Thr
        195                 200                 205

Val Ala Asp Ile Glu Pro Lys Phe Asp Arg Leu Ile Phe Phe Trp Ser
210                 215                 220

Asp Ile Arg Asn Pro His Glu Val Gln Pro Ala His Arg Thr Arg Tyr
225                 230                 235                 240

Ala Ile Thr Val Trp Tyr Phe Asp Ala Lys Glu Arg Glu Glu Ala Leu
                245                 250                 255

Ile Arg Ala Lys Leu Glu Asn Ser Lys Thr Asn Asn Leu Ala Ala Gln
            260                 265                 270

Ala Gln Ala Gln Gln Ala Glu Pro Asp Ser Thr Thr Thr Pro Pro Ala
        275                 280                 285

Ala Pro Ala Ser Ser Ala Ser Ser Leu Pro Val Ser Met Ser Thr Gly
290                 295                 300

Thr Gly Ala Leu Asn Ala Asn Val Ser Ser Asn Ser Cys Ala Thr Ser
305                 310                 315                 320

Ser Glu Ile Cys Thr
            325

```
<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Synthetic
      sequence derived from HIF-a ODD domain.

<400> SEQUENCE: 5

Asp Leu Asp Leu Glu Ala Leu Ala Pro Tyr Ile Pro Ala Asp Asp Asp
 1               5                  10                  15

Phe Gln Leu
```